(12) United States Patent
Elam et al.

(10) Patent No.: US 6,845,147 B2
(45) Date of Patent: Jan. 18, 2005

(54) SCATTER SPECTRA METHOD FOR X-RAY FLUORESCENT ANALYSIS WITH OPTICAL COMPONENTS

(75) Inventors: William T. Elam, Redmond, WA (US); Joseph A. Nicolosi, Bardonia, NY (US); Robert B. Shen, South Barrington, IL (US); Bruce E. Scruggs, Englewood, NJ (US)

(73) Assignee: EDAX Inc., Mahwah, NJ (US)

( * ) Notice: Subject to any disclaimer, the term of this patent is extended or adjusted under 35 U.S.C. 154(b) by 0 days.

(21) Appl. No.: 10/464,073

(22) Filed: Jun. 17, 2003

(65) Prior Publication Data

US 2004/0066886 A1 Apr. 8, 2004

Related U.S. Application Data

(60) Provisional application No. 60/389,248, filed on Jun. 17, 2002.

(51) Int. Cl.[7] ............................................. G01N 23/201
(52) U.S. Cl. ........................................ 378/86; 378/207
(58) Field of Search .............................. 378/86–89, 207

(56) References Cited

U.S. PATENT DOCUMENTS 6,345,194 B1 * 2/2002 Nelson et al. .............. 600/425

OTHER PUBLICATIONS

Tertian et al., Chapter 3. Excitation Sources. Spectral Distributions from X–Ray Tubes, *Principles of Quantitative X–Ray Fluorescence Analysis*, 1982, pp. 36–48, Heyden & Son, Ltd, London.
Tertian et al., Chapter 4. Calculation of Theoretical Fluorescence Intensities, *Principles of Quantitative X–Ray Fluorescence Analysis*, 1982, pp. 51–69, Heyden & Son, Ltd, London.
Tertian et al., Chapter 9. The Fundamental Parameter Method, *Principles of Quantitative X–Ray Fluorescence Analysis*, 1982, pp. 122–130, Heyden & Son, Ltd, London.
Bilbrey et al., "Comparison of Fundamental Parameters Programs for Quantitative X–Ray Fluorescence Spectrometry," *X–Ray Spectrometry*, 1988, pp. 63–73, vol. 17.
Tao et al., "An Attempt at Improving the Accuracy of Calculated Relative Intensities from Theory in X–Ray Fluorescence Spectrometry," *X–Ray Spectrometry*, 1998, pp. 357–366, vol. 27.
De Boer et al., "How Accurate is the Fundamental Parameter Approach? XRF Analysis of Bulk and Multilayer Samples," *X–Ray Spectrometry*, 1993, pp. 33–38, vol. 22.

(List continued on next page.)

*Primary Examiner*—Craig E. Church
*Assistant Examiner*—Jurie Yun
(74) *Attorney, Agent, or Firm*—Webb Ziesenheim Logsdon Orkin & Hanson, P.C.

(57) ABSTRACT

A method of measuring the transfer function of an X-ray optical component over a wide range of X-ray energies, which includes the steps of:
  using an X-ray optical component between an X-ray source and a scattering target to obtain a first scatter spectrum;
  obtaining a second scatter spectrum from the same or a similar target without the X-ray optical component between the X-ray source and the scattering target; and
  calculating the transfer function by the ratio of the first scatter spectrum to the second scatter spectrum. The method can be used to improve the accuracy of X-ray quantitative methods in an apparatus where an X-ray optical component is used between the X-ray source and the specimen to be investigated by utilizing the method described above.

20 Claims, 4 Drawing Sheets

OTHER PUBLICATIONS

Pella et al., "Intercomparison of Selected Semi–empirical and Fundamental Parameter Interelement Correction Methods in X–Ray Spectrometry," *X–Ray Spectrometry*, 1982, pp. 167–169, vol. 11, No. 4.

Elam et al., "A New Atomic Database for X–Ray Spectroscopic Calculations," *Radiation Physics and Chemistry*, 2002, pp. 121–128, vol. 63.

Ebel, "X–Ray Tube Spectra," *X–Ray Spectrometry*, 1999, pp. 255–266, vol. 28.

Finkelshtein et al., "Calculation of X–Ray Tube Spectral Distributions," *X–Ray Spectrometry*, 1999, pp. 27–32, vol. 28.

\* cited by examiner

SCATTER SPECTRA METHOD FOR X-RAY FLUORESCENT ANALYSIS WITH OPTICAL COMPONENTS

CROSS-REFERENCE TO RELATED APPLICATION

This application claims the benefit of United States Provisional Application No. 60/389,248, filed Jun. 17, 2002, entitled "Scatter Spectra Method for X-Ray Fluorescent Analysis with Optical Components," which is hereby incorporated by reference.

BACKGROUND OF THE INVENTION

1. Field of the Invention

The present invention is directed to a method of performing standardless quantitative analysis using X-ray fluorescence.

2. Description of the Prior Art

X-ray fluorescence (XRF) instruments are a standard means of determining information, such as plating thicknesses, composition, and elemental makeup. In XRF measurement, X-rays impinge on a sample, causing its atoms to emit fluorescence radiation. An energy or wavelength discriminating X-ray detector records the radiation. The reading is amplified and digitized to be evaluated by measurement and analysis software.

The raw measurement data is in the form of a fluorescence spectrum that characterizes the test sample. The measurement challenge is not necessarily to determine which elements are present in the sample, but rather in what quantity they are present. Consequently, analysis of the spectrum has to focus on the intensity of the fluorescence radiation.

In the field of XRF spectroscopy, quantitative analysis is typically performed by either of two methods: 1) using standards of known concentration for calibration of the measured X-ray intensities with unknown samples; and 2) calculating the concentrations directly from the measured intensities using the Fundamental Parameters Method.

Of the techniques used to analyze XRF measurement data, the Fundamental Parameters Method significantly improves the capability of the XRF instrument. In XRF analysis, the traditional Fundamental Parameters Method results in an evaluation based on mathematical formulation of the elemental physical processes, as opposed to generating an empirical model using calibration standards.

The Fundamental Parameters Method of analysis of XRF measurements has been used to obtain data with and without capillary optics. However, the Fundamental Parameters Method is limited in its application because it is difficult to use with capillary or other optical components in the beam path. When capillary or other optical components are in the beam path, the optical component modifies the energy spectrum of the X-ray beam in an unpredictable fashion. The X-ray beam modification reduces the accuracy of the method to less than is typically required for successful analysis of XRF measurements.

Prior attempts to use the Fundamental Parameters Method with optical components required the use of a large number of empirical correction factors that were determined via the use of standard samples. In prior art methods, the sensitivity factors are adjusted, but the correct excitation spectra is not calculated. Further, in prior methods, new empirical correction factors are needed for each measurement condition and sample matrix.

It would be desirable then to provide a method of making XRF measurements without the need to determine and utilize a large number of empirical correction factors when optical components are used with an XRF instrument.

SUMMARY OF THE INVENTION

The present invention is directed to a method of measuring the transfer function of an X-ray optical component over a wide range of X-ray energies. The method includes the steps of:

using an X-ray optical component between an X-ray source and a scattering target to obtain a first scatter spectrum;

obtaining a second scatter spectrum from the same or a similar target without the X-ray optical component between the X-ray source and the scattering target; and calculating the transfer function by the ratio of the first scatter spectrum to the second scatter spectrum.

The present invention is also directed to a method of improving the accuracy of X-ray quantitative methods in an apparatus where an X-ray optical component is used between the X-ray source and the specimen to be investigated by utilizing the method described above.

The present invention is further directed to a method of determining the correct incident energy spectrum when optical components are in the beam path of an X-ray fluorescence instrument. The method includes the steps of:

(A) determining a transfer function for the optical component by;
   (i) making a scatter measurement over the maximum operating energy range with the optical component in place;
   (ii) making a scatter measurement over the maximum operating energy range in (i) without the optical component in place; and
   (iii) calculating the transfer function by the ratio of scatter spectrum intensity in (ii) to the scatter spectrum in (i) as a function of energy;

(B) obtaining the incident spectrum over a given energy range without the optical component in place; and (C) correcting the incident spectrum in (B) by applying the transfer function in (A) to create the correct incident energy spectrum for the instrument with the optical component in place.

The present invention is additionally directed to a method of standardless quantitative analysis where the correct incident energy spectrum described above is analyzed using the Fundamental Parameters Method to determine the composition and elemental makeup of a sample.

These and other advantages of the present invention will be clarified in the description of the preferred embodiment taken together with the attached drawings in which like reference numerals represent like elements throughout.

DETAILED DESCRIPTION OF THE PREFERRED EMBODIMENTS

Figure 1:
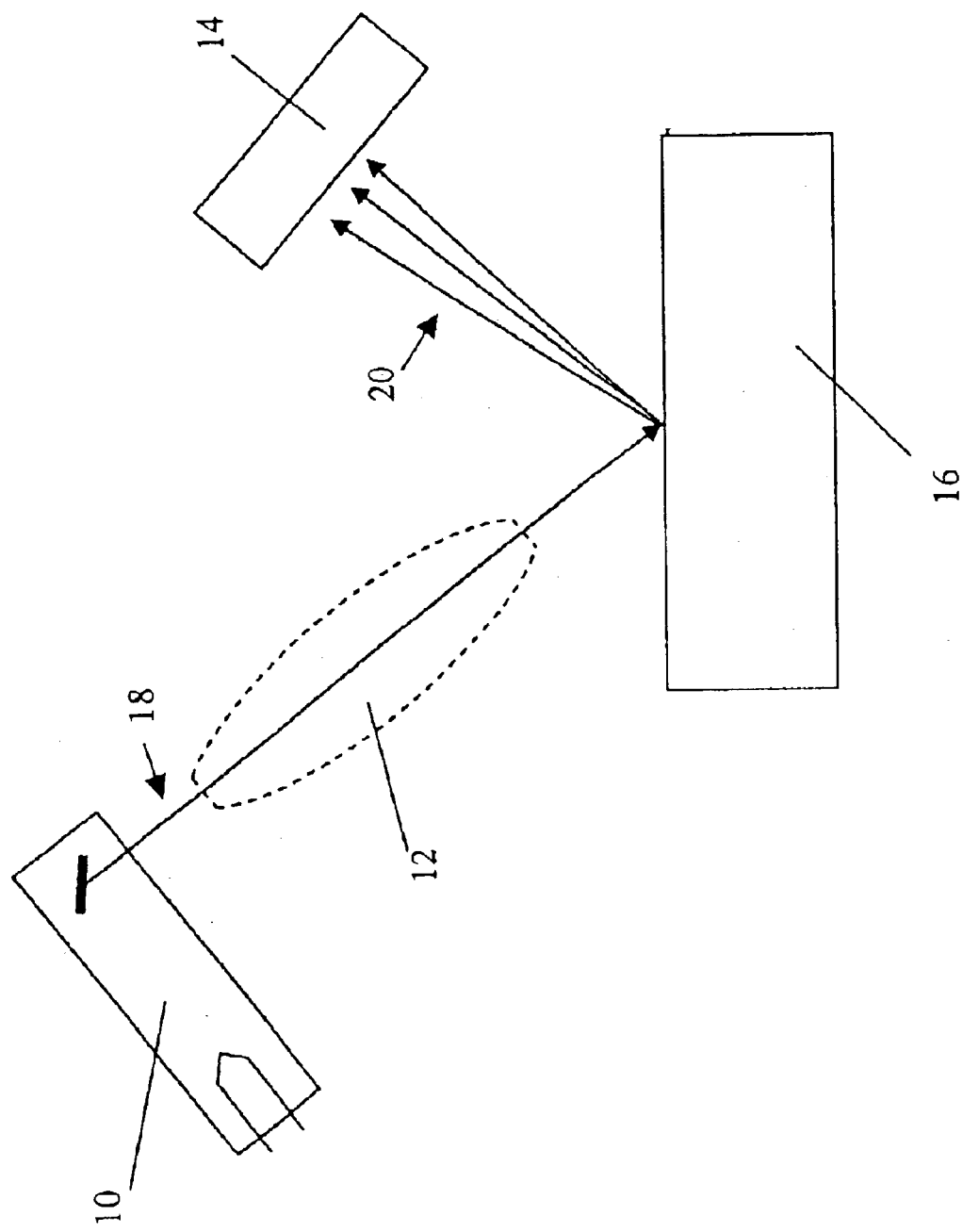
FIG. 1 is a depiction of an X-ray fluorescence spectrometer capable of utilizing the method of the present invention.

As used herein, "X-ray fluorescence" refers to spectra obtained by impinging X-rays on a sample, causing its atoms to emit fluorescence radiation, which is subsequently measured by a detector and recorded as count intensity as a function of energy.

As used herein, "X-ray absorption fine structure" refers to the small modulations in the X-ray absorption of an element, comprising about 4% of the total absorption, and caused by the aggregate effect of nearby atoms when the element is in solid form, whether by itself or in combination with other elements.

As used herein, the term "X-ray absorption near edge structure" refers to the increases and decreases in the X-ray absorption of an element within about 50 electron volts of the X-ray absorption edges of the element, caused by the particular chemical environment of the element.

As used herein, the term "theoretical standards" refers to reference standards used for calibration of an analytical instrument which are produced from mathematical models rather than measurements.

As used herein, the term "theoretical influence coefficients" refers to mathematical coefficients, which quantify the effect on the X-ray intensity of an element due to other elements and which are obtained from mathematical models without any measurements.

As indicated above, the present invention provides a method of measuring the transfer function of an X-ray optical component over a wide range of X-ray energies including the steps of:

- using an X-ray optical component between an X-ray source and a scattering target to obtain a first scatter spectrum;
- obtaining a second scatter spectrum from the same or a similar target without the X-ray optical component between the X-ray source and the scattering target; and
- calculating the transfer function by the ratio of the first scatter spectrum to the second scatter spectrum.

Any suitable optical components can be used in the present invention. Suitable optical components include, but are not limited to, X-ray optical components, such as a monocapillary, a polycapillary bundle, a monolithic polycapillary, a reflective surface, a diffraction element, and an X-ray optical component which modifies the exciting or input spectrum generated by an X-ray source.

In an embodiment of the present invention, the transfer function is used to characterize the influence of an X-ray optical component on the exciting spectrum of an apparatus.

When an X-ray optical component is used, it can be contained or used within or as part of any suitable apparatus. Suitable apparatus that can include the X-ray optical component include, but are not limited to, an X-ray fluorescence analyzer, an X-ray diffraction analyzer, an X-ray absorption analyzer, and an X-ray transmission analyzer.

An embodiment of the present invention is directed to a method for improving the accuracy of X-ray quantitative methods in an apparatus where an X-ray optical component is used between the X-ray source and the specimen to be investigated. The method includes the steps of (a) determining a transfer function for the X-ray optical component as described above; and (b) applying the transfer function to the incident X-ray spectra used in a quantitative method to obtain a corrected incident spectra.

Any suitable X-ray quantitative method may be used in the present invention. Suitable X-ray quantitative methods that can be used include, but are not limited to, the fundamental parameters method, X-ray absorption spectroscopy, X-ray absorption fine structure, X-ray absorption near edge structure, X-ray diffraction, X-ray transmission, and a standardless method.

In an embodiment of the present invention, the X-ray quantitative method uses theoretical standards for calibration based on knowledge of the exciting X-ray spectrum from the X-ray source.

In a further embodiment of the present invention, the X-ray quantitative method uses theoretical influence coefficients calculated using knowledge of the exciting X-ray spectrum.

In an additional embodiment of the present invention, the X-ray quantitative method comprises a method that relies on knowledge of the exciting X-ray spectrum.

In a particular embodiment of the present invention, the inventive method is used as part of a method of measuring the thickness of a coating on a substrate. In this embodiment, the step of correcting the incident X-ray spectra can be used to determine the thickness of a coating film.

In a certain embodiment of the invention, the inventive method is used as part of a method of performing a compositional analysis of a sample. In this embodiment, the step of correcting the incident X-ray spectra can be used to perform a compositional analysis of a sample.

In a further particular embodiment of the present invention, the method of the present invention is used to determine the correct incident energy spectrum when optical components, such as capillary or other optics, are in the beam path of X-ray fluorescence (XRF) instruments. The method is especially useful in analyzing XRF measurements via the Fundamental Parameters Method. The present method further improves the analytical accuracy of standardless quantitative analysis and facilitates instrument adjustment and calibration when optical components are changed.

The Fundamental Parameters Method uses a data file of X-ray absorption coefficients, fluorescence yields, and other "fundamental" parameters of various elements of interest in well-established equations that model the fluorescence process. The spectrum of X-rays emitted from a sample is analyzed in order to quantify the composition of the material whose X-ray lines were measured. The different elements in the sample have different X-ray absorption properties, and so the line intensity for an element will be affected by the concentrations of all elements present in the sample. When applied to the correct incident energy spectrum, the Fundamental Parameters Method is able to identify and provide relative ratios of the elements in a sample.

Figure 2:
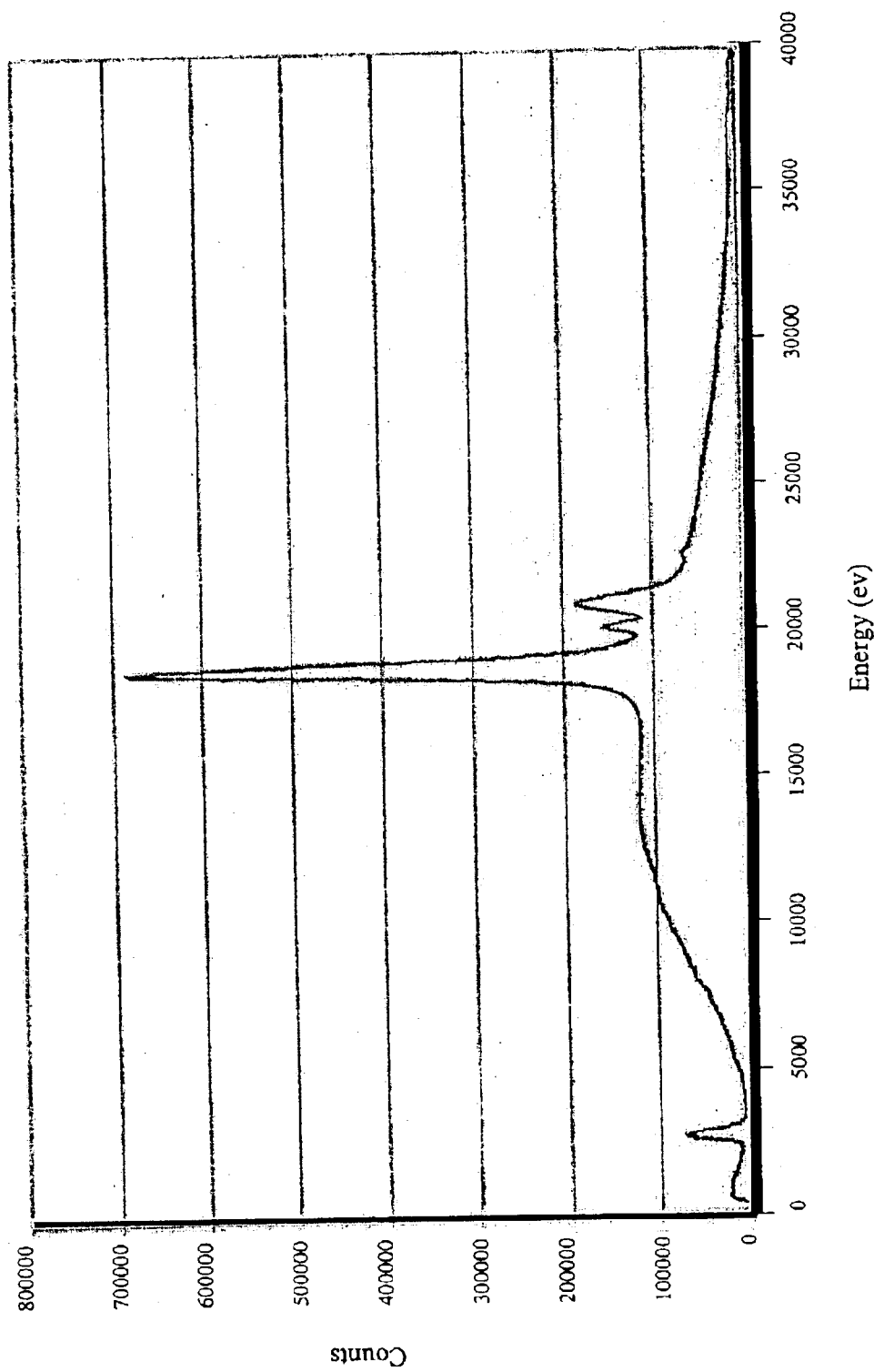
FIG. 2 shows a scatter spectrum obtained without using an optical component.
Figure 3:
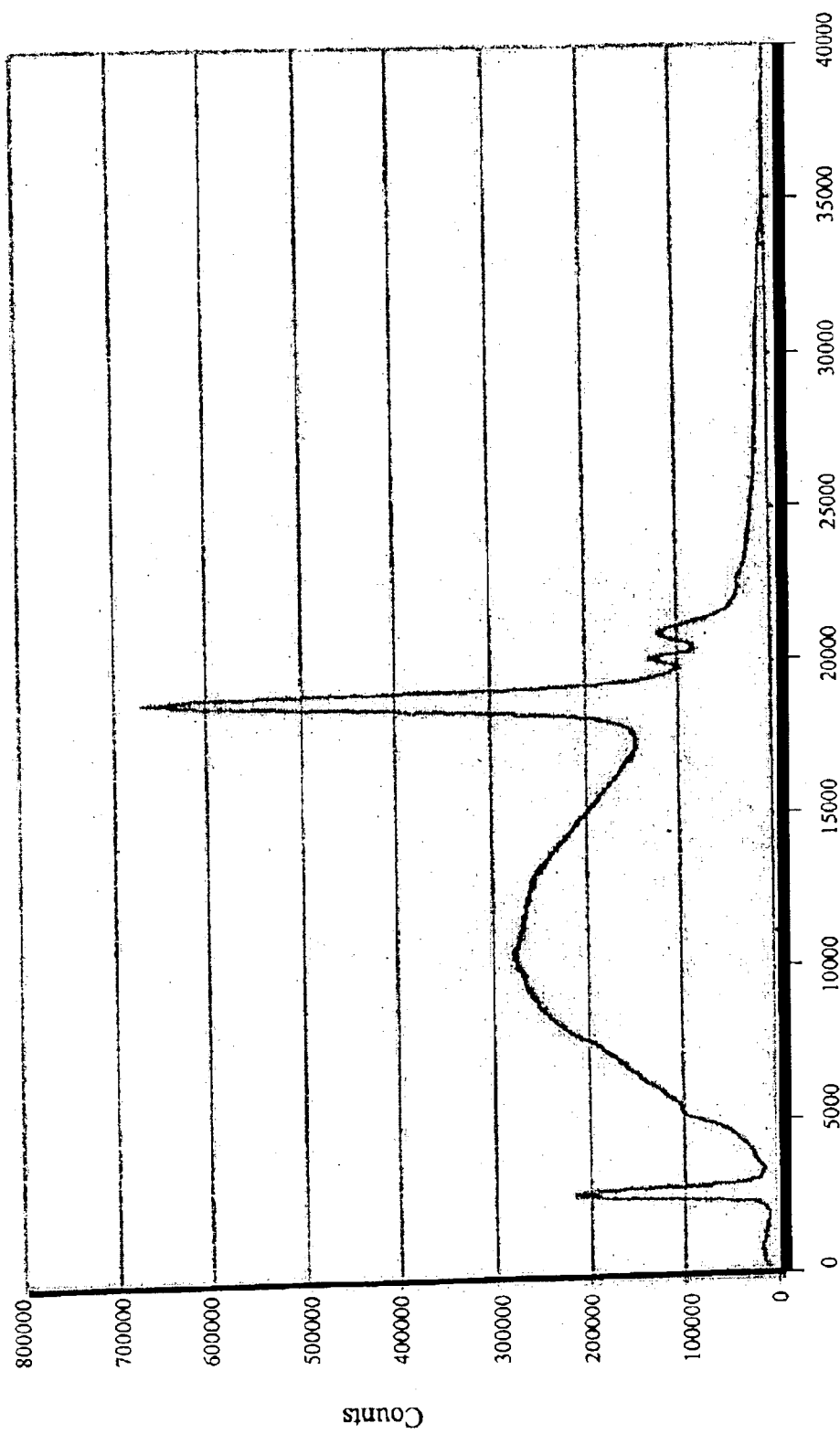
FIG. 3 shows a scatter spectrum obtained using an optical component, showing the alteration of the energy spectrum by the optical component.

In an embodiment of the present invention, a number of optical components (non-limiting examples of such being collimators, apertures, capillary optics, and filters) may be used in XRF spectrometers between the X-ray tube and the sample to condition the beam incident on the sample. In the present invention, the energy response of one or more of these optical components is determined by a transfer function at several energies. This function can be measured via scatter from a light element plate (such as a paraffin wax block) in place of the sample. When the scatter measurement is made over the entire operating energy range, both with (see FIG. 3) and without (see FIG. 2.) the optical component in place, and calculating the ratio as a function of energy (see FIG. 4), the proper transfer function can be obtained for any optical component. The transfer function may then be used, for example, to more accurately determine the spectral characteristics of the X-ray beam incident on the sample.

This overcomes the problem in the prior art, where a large number of empirical correction factors were determined on various standard samples in order to use the Fundamental Parameters Method. In the present invention, the incident spectrum may be used for analyzing measurements made with XRF instruments to obtain, for example, accurate compositions of the samples under investigation or determining optimum excitation conditions to be used for a particular type of sample. A depiction of the present method is shown in FIG. 1.

Figure 4:
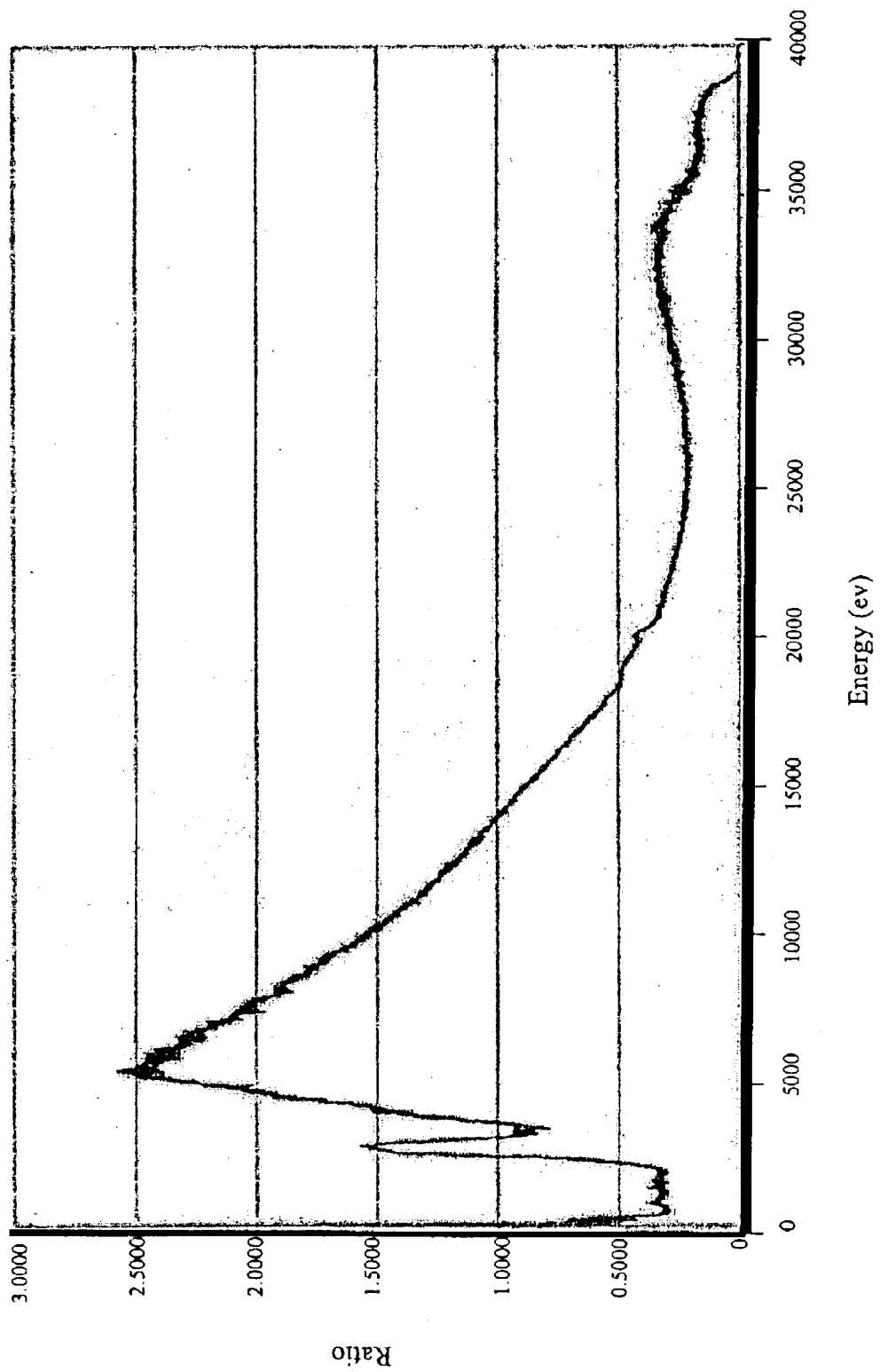
FIG. 4 shows a transfer function as used in the present invention depicting the ratio of scatter spectrum intensity with and without an optical component as a function of energy, which characterizes the influence of the optical component under a wide range of operating conditions.

An example of an embodiment of the present invention is shown in FIG. 1, where an X-ray tube 10 emits an X-ray beam 18 (incident beam) in the general direction of a scatter block 16. X-ray beam 18 passes through an optical component 12, impinges on scatter block 16, and forms a scatter pattern 20. The scatter pattern 20 is measured over the entire operating energy range by detector 14. The scatter measurement is made over the entire operating energy range, with (FIG. 3) and without (FIG. 2) the optical component in place, and a ratio is calculated as a function of energy as shown in FIG. 4. The transfer function (FIG. 4) is then applied at any given operating energy, with the optical component in place, to more accurately determine the spectral characteristics of the X-ray beam incident on the sample. An accurate composition of the sample can be determined from the corrected incident spectra and application of the Fundamental Parameters Method. The transfer function in FIG. 4, which is applied to the incident beam, is the ratio of the spectra in FIG. 2 to the spectra in FIG. 3.

Direct measurement of the capillary optic transfer function without using the scatter and ratio method of this invention is very difficult or impossible because the detector saturates when measuring the spectrum directly, and the atmosphere and other absorbers in the beam modify the spectrum. The present invention overcomes both of these limitations by enabling determination of the correct excitation spectrum incident on the sample to be used in the fundamental parameters calculation. The results are more accurate than those obtained by other methods.

An embodiment of the present invention includes a method of measuring the energy response transfer function of capillary or other optical components in the X-ray beam path rather than applying empirical estimates of correction factors or requiring measurements of the direct incident beam.

A further embodiment of the present invention facilitates determination of the correct incident X-ray spectra for any optical component placed between the X-ray tube and a sample. Further, the present invention improves the accuracy of the standardless Fundamental Parameters Method when used with capillary optics to better than 1%. The geometric arrangement of the spectrometer does not need to be reconfigured to measure the incident beam. There is no need to determine empirical factors to correct calculations on concentrations for different sample types. The present method may be used without any empirically measured correction factors and over a wide variety of measurement conditions and sample compositions without recalibration or remeasurement of the optical component transfer function.

Thus, the method of the present invention provides improved efficiency by applying a transfer function determined at a maximum operating energy range over the entire operating range. This is a marked improvement over prior art attempts to use the Fundamental Parameters Method with optical components, which required the use of a large number of empirical correction factors that were determined via the use of standard samples. In prior art methods, the sensitivity factors were adjusted, but the correct excitation spectra was not calculated. Further, in prior methods, new empirical correction factors were needed for each measurement condition and sample matrix. The present invention solves these problems because the inventive method may be used without any empirically measured correction factors and over a wide variety of measurement conditions and sample compositions without recalibration or remeasurement of the optical component transfer function.

Those skilled in the art will recognize that changes may be made to the embodiments described above without departing from the broad inventive concept thereof. It is understood, therefore, that this invention is not limited to the particular embodiments disclosed, but it is intended to cover modifications that are within the spirit and scope of the invention.

We claim:

1. A method of measuring the transfer function of an X-ray optical component over a wide range of X-ray energies comprising:
    using an X-ray optical component to convey X-rays from an X-ray source to a scattering target to obtain a first scatter spectrum;
    obtaining a second scatter spectrum from the same or a similar target without the X-ray optical component between the X-ray source and the scattering target; and
    calculating the transfer function by the ratio of the first scatter spectrum to the second scatter spectrum.

2. The method of claim 1, wherein the X-ray optical component is selected from the group consisting of collimators, apertures, capillary optics, filters, a monocapillary, a polycapillary bundle, a monolithic polycapillary, a reflective surface, a diffraction element, and an X-ray optical component which modifies the exciting or input spectrum generated by the X-ray source.

3. The method of claim 1, wherein the ratio is used to characterize the influence of the X-ray optical component on the exciting spectrum of the apparatus.

4. The method of claim 1, wherein the X-ray optical component is contained within an apparatus selected from the group consisting of an X-ray fluorescence analyzer, an X-ray diffraction analyzer, an X-ray absorption analyzer, and an X-ray transmission analyzer.

5. A method for improving the accuracy of X-ray quantitative methods in an apparatus where an X-ray optical component is used between the X-ray source and the specimen to be investigated comprising:
    (a) determining a transfer function for the X-ray optical component by:
        obtaining a first scatter spectrum using an X-ray optical component to convey X-rays from an X-ray source to a scattering target;
        obtaining a second scatter spectrum from the same or a similar target without the X-ray optical component between the X-ray source and the scattering target; and
        calculating the transfer function by the ratio of the first scatter spectrum to the second scatter spectrum; and
    (b) obtaining the incident spectrum over a given energy range without the optical component in place; and
    (c) correcting the incident spectrum in (b) by applying the transfer function in (a) to create the correct incident energy spectrum for the instrument with the optical component in place.

6. The method of claim 5, wherein the apparatus is selected from the group consisting of an X-ray fluorescence analyzer, an X-ray diffraction analyzer, an X-ray absorption analyzer, and an X-ray transmission analyzer.

7. The method of claim 5, wherein the X-ray quantitative method is selected from the group consisting of the fundamental parameters method, X-ray absorption spectroscopy, X-ray absorption fine structure, X-ray absorption near edge structure, X-ray diffraction, X-ray transmission, and a standardless method.

8. The method of claim 5, wherein the X-ray quantitative method uses theoretical standards for calibration based on knowledge of the exciting X-ray spectrum from the X-ray source.

9. The method of claim 8, wherein the X-ray quantitative method uses theoretical influence coefficients calculated using knowledge of the exciting X-ray spectrum.

10. The method of claim 8, wherein the X-ray quantitative method comprises a method which relies on knowledge of the exciting X-ray spectrum.

11. A method of measuring the coating thickness of a coating film comprising the method of claim 5.

12. A method of performing a compositional analysis of a sample comprising the method of claim 5.

13. The method of claim 5, further comprising the step of analyzing the corrected X-ray spectra to determine the thickness of a coating film.

14. The method of claim 5, further comprising the step of analyzing the corrected X-ray spectra to perform a compositional analysis of a sample.

15. A method of determining a correct incident energy spectrum from an X-ray fluorescence instrument when one or more optical components are in the X-ray beam path between a source and sample comprising:
   (a) determining a transfer function for each optical component by:
      (i) making scatter measurements of X-rays from the sample over a maximum operating energy range with each optical component in place;
      (ii) making scatter measurements of X-rays from the sample over the maximum operating energy range in (i) without an optical component in place; and
      (iii) calculating the transfer function for each optical component by the ratio of scatter spectrum intensity in (ii) to the scatter spectrum in (i) as a function of energy;
   (b) obtaining an incident spectrum over a given energy range without the optical component in place; and
   (c) correcting the incident spectrum in (b) by applying one or more of the transfer functions in (a) to create the correct incident energy spectrum for the instrument with one or more optical components in place.

16. The method of claim 15, wherein the optical components are selected from the group consisting of collimators, apertures, capillary optics, filters, a monocapillary, a polycapillary bundle, a monolithic polycapillary, a reflective surface, a diffraction element, and an X-ray optical component which modifies the exciting or input spectrum generated by the X-ray source.

17. The method of claim 15, wherein the X-ray fluorescence instrument is selected from the group consisting of an X-ray fluorescence analyzer, an X-ray diffraction analyzer, an X-ray absorption analyzer, and an X-ray transmission analyzer.

18. A method of standardless quantitative analysis of a sample comprising:
   (A) determining a correct incident energy spectrum from an X-ray fluorescence instrument when one or more optical components are in the X-ray beam path comprising:
      (a) determining a transfer function for each optical component by:
         (i) making scatter measurements of X-rays from the sample over a maximum operating energy range with each optical component in place;
         (ii) making scatter measurements of X-rays from the sample over the maximum operating energy range in (i) without an optical component in place; and
         (iii) calculating the transfer function for each optical component by the ratio of scatter spectrum intensity in (ii) to the scatter spectrum in (i) as a function of energy;
      (b) correcting an incident spectrum calculated using a Fundamental Parameters Method by applying one or more of the transfer functions in (a) to create the correct incident energy spectrum for the instrument with one or more optical components in place; and
   (B) obtaining the X-ray fluorescence spectrum from the sample with the optical component in place; and
   (C) analyzing the X-ray fluorescence spectrum in (B) using the corrected incident energy spectrum in (A) with the Fundamental Parameters Method to determine the composition and elemental makeup of the sample.

19. The method of claim 18, wherein the optical components are selected from the group consisting of collimators, apertures, capillary optics, filters, a monocapillary, a polycapillary bundle, a monolithic polycapillary, a reflective surface, a diffraction element, and an X-ray optical component which modifies the exciting or input spectrum generated by the X-ray source.

20. The method of claim 19, wherein the X-ray fluorescence instrument is selected from the group consisting of an X-ray fluorescence analyzer, an X-ray diffraction analyzer, an X-ray absorption analyzer, and an X-ray transmission analyzer.

* * * * *